(12) United States Patent
Horiuchi et al.

(10) Patent No.: US 8,877,354 B2
(45) Date of Patent: Nov. 4, 2014

(54) HETEROCYCLIC COMPOUND AND ORGANIC LIGHT-EMITTING DEVICE USING THE SAME

(75) Inventors: Takayuki Horiuchi, Tokyo (JP); Jun Kamatani, Tokyo (JP); Akihito Saitoh, Gotemba (JP)

(73) Assignee: Canon Kabushiki Kaisha, Tokyo (JP)

( * ) Notice: Subject to any disclaimer, the term of this patent is extended or adjusted under 35 U.S.C. 154(b) by 448 days.

(21) Appl. No.: 13/391,268

(22) PCT Filed: Aug. 5, 2010

(86) PCT No.: PCT/JP2010/004946
§ 371 (c)(1),
(2), (4) Date: Feb. 17, 2012

(87) PCT Pub. No.: WO2011/024391
PCT Pub. Date: Mar. 3, 2011

(65) Prior Publication Data
US 2012/0153270 A1    Jun. 21, 2012

(30) Foreign Application Priority Data

Aug. 25, 2009    (JP) .................. 2009-194110

(51) Int. Cl.
*H01L 51/54* (2006.01)
*C09K 11/06* (2006.01)
*C07D 471/04* (2006.01)
*H01L 51/00* (2006.01)
*H05B 33/22* (2006.01)
*H01L 51/50* (2006.01)

(52) U.S. Cl.
CPC .......... *C07D 471/04* (2013.01); *H01L 51/0072* (2013.01); *H01L 51/5048* (2013.01); *C09K 2211/1029* (2013.01); *H01L 51/0071* (2013.01); *H05B 33/22* (2013.01); *C09K 11/06* (2013.01); *Y10S 428/917* (2013.01)
USPC ............. 428/690; 428/917; 546/70; 313/506; 257/40; 257/E51.026

(58) Field of Classification Search
None
See application file for complete search history.

(56) References Cited

U.S. PATENT DOCUMENTS

2008/0122344 A1    5/2008 Shin

FOREIGN PATENT DOCUMENTS

| JP | 2004-043349 A | 2/2004 |
|---|---|---|
| JP | 2004-043349 A | 2/2004 |
| JP | 2009-057445 A | 3/2009 |
| JP | 2009-161464 A | 7/2009 |
| WO | 2007/064484 A2 | 6/2007 |
| WO | 2007/064493 A1 | 6/2007 |
| WO | 2007/127069 A1 | 11/2007 |
| WO | 2007/130263 A1 | 11/2007 |
| WO | 2008/133483 A2 | 11/2008 |
| WO | 2008/142047 A | 11/2008 |
| WO | 2009/008311 A1 | 1/2009 |
| WO | 2009/008354 A1 | 1/2009 |

OTHER PUBLICATIONS

Journal of Health Science, Mar. 2, 2007, vol. 53, No. 3, pp. 320-324.
Yamada et al., Nitrogen-substitution effects on the mutagenicity and cytochrome P450 isoform-selectivity of chrysene analog, Mutation Research, 2005, 586, 87-95.
Hakura et al., Modification of mutagenicity by fluorine-substitution on diazachrysene, Journal of Health Science, 2007, vol. 53, No. 3, pp. 320-324.

*Primary Examiner* — Andrew K Bohaty
(74) *Attorney, Agent, or Firm* — Canon U.S.A., Inc. IP Division

(57) ABSTRACT

An organic light-emitting device includes an anode, a cathode, and an organic compound layer interposed between the anode and the cathode. The organic compound layer contains a heterocyclic compound represented by general formula [1]:

(wherein $R_1$ and $R_2$ each independently represent a hydrogen atom, a substituted or unsubstituted alkyl group, a substituted or unsubstituted aryl group having three or less rings, or a substituted or unsubstituted heterocyclic group having three or less rings; $R_1$ and $R_2$ may be the same as or different from each other; $R_3$ and $R_4$ each independently represent a hydrogen atom, a substituted or unsubstituted aryl group having three or less rings, or a substituted or unsubstituted heterocyclic group having three or less rings; one of $R_3$ and $R_4$ represents a substituted or unsubstituted aryl group having three or less rings or a substituted or unsubstituted heterocyclic group having three or less rings; and $R_3$ and $R_4$ may be the same as or different from each other).

[Chem. 1]

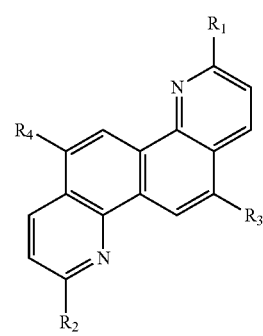

[1]

5 Claims, 1 Drawing Sheet

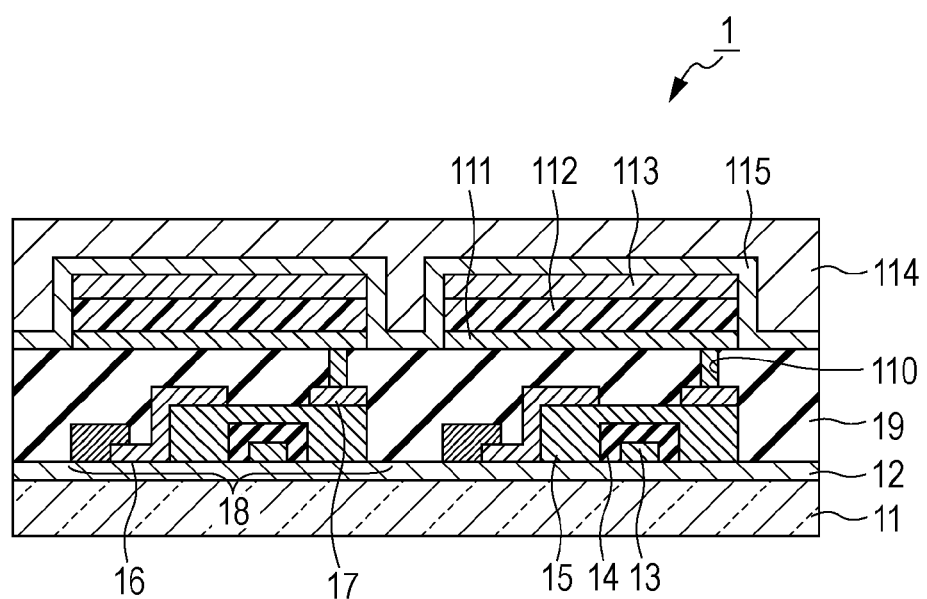

HETEROCYCLIC COMPOUND AND ORGANIC LIGHT-EMITTING DEVICE USING THE SAME

TECHNICAL FIELD

The present invention relates to a heterocyclic compound and an organic light-emitting device using the heterocyclic compound.

BACKGROUND ART

Organic light-emitting devices are a type of light-emitting device that includes a thin film containing a fluorescent organic compound interposed between an anode and a cathode. When electrons and holes are injected from the respective electrodes, excitons of the fluorescent compound are generated and the organic light-emitting device emits light as the excitons return to their ground state.

The recent advancement of organic light-emitting devices has been remarkable. Organic light-emitting devices make it possible to produce thin and light-weight light-emitting devices that have high luminance at a low application voltage and a wide variety of emission wavelengths and display rapid response. This suggests that the organic light-emitting devices can be used in a wide variety of usages.

However, presently, there remains room for improvements. To be more specific, emitted light needs to have a higher luminance and the optical conversion efficiency needs to be increased for practical applications. Moreover, improvements are needed in terms of durability, such as changes with time caused by long use and deterioration caused by oxygen-containing atmospheric gas and humidity. In order for the devices to be applicable to displays of portable appliances, the power consumption of the devices needs to be low. In particular, electron injection/transport materials which are constituent materials of electron injection layers and electron transport layers affect the driving voltage, the emission efficiency, and the lifetime of organic light-emitting devices. Thus, research and development on the electron injection/transport materials have been actively pursued. However, the current situation does not sufficiently address the aforementioned challenges. When devices are used as constituent parts of full color displays, deterioration of blue pixels proceeds fastest. Thus, materials that increase the efficiency and extend the lifetimes of blue light-emitting devices are desired.

One of the approaches to address these challenges is the proposal of organic compounds having phenanthroline and anthracene backbones. Attempts have been made to use such organic compounds as the constituent materials of the electron injection layer and the electron transport layer of an organic light-emitting device (refer to PTL 1 to PTL 4). However, their emission hue, emission efficiency, luminance, and durability need to be improved further.

NPL 1 proposes an organic compound having a 4,10-diazachrysene backbone and a synthetic method therefor.

CITATION LIST

Patent Literature

PTL 1: International Publication 2007/064484
PTL 2: International Publication 2007/064493
PTL 3: International Publication 2007/127069
PTL 4: International Publication 2007/130263

Non Patent Literature

NPL 1: Mutation Research, 586, 87-95 (2005)

SUMMARY OF INVENTION

An aspect of the present invention provides a heterocyclic compound represented by general formula [1]:

[Chem. 1]

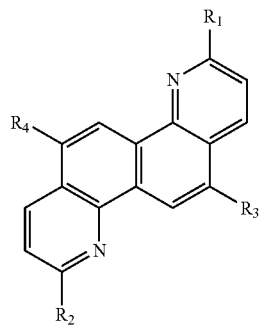

[1]

In formula [1], $R_1$ and $R_2$ each independently represent a hydrogen atom, a substituted or unsubstituted alkyl group, a substituted or unsubstituted aryl group having three or less rings, or a substituted or unsubstituted heterocyclic group having three or less rings; $R_1$ and $R_2$ may be the same as or different from each other; $R_3$ and $R_4$ each independently represent a hydrogen atom, a substituted or unsubstituted aryl group having three or less rings, or a substituted or unsubstituted heterocyclic group having three or less rings; one of $R_3$ and $R_4$ represents a substituted or unsubstituted aryl group having three or less rings or a substituted or unsubstituted heterocyclic group having three or less rings; and $R_3$ and $R_4$ may be the same as or different from each other.

BRIEF DESCRIPTION OF DRAWINGS

FIG. 1 is a cross-sectional view of an example of an image display apparatus equipped with an organic light-emitting device according to one embodiment of the present invention.

DESCRIPTION OF EMBODIMENTS

The present invention will now be described in detail through embodiments. A heterocyclic compound according to an embodiment of the present invention is first described. The heterocyclic compound of this embodiment is represented by general formula [1] below.

[Chem. 2]

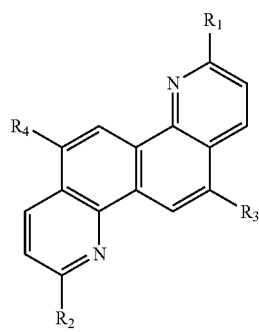

[1]

In formula [1], $R_1$ and $R_2$ each independently represent a hydrogen atom, a substituted or unsubstituted alkyl group, a substituted or unsubstituted aryl group having three or less rings, or a substituted or unsubstituted heterocyclic group having three or less rings.

Examples of the alkyl groups represented by $R_1$ and $R_2$ include, but are not limited to, a methyl group, an ethyl group, a normal propyl group, an isopropyl group, a normal butyl group, a tertiary butyl group, a secondary butyl group, an octyl group, a 1-adamantyl group, and a 2-adamantyl group.

Examples of the aryl group having three or less rings represented by $R_1$ and $R_2$ include, but are not limited to, a phenyl group, a naphthyl group, an anthryl group, a phenanthryl group, an indenyl group, a biphenyl group, a terphenyl group, and a fluorenyl group.

Examples of the heterocyclic group having three or less rings represented by $R_1$ and $R_2$ include, but are not limited to, a pyridyl group, a quinolyl group, an oxazolyl group, an oxadiazolyl group, a thiazolyl group, a thiadiazolyl group, a carbazolyl group, an acridinyl group, and a phenanthrolyl group.

Examples of the substituents that may be contained in the alkyl group, the aryl group, and the heterocyclic group include, but are not limited to, alkyl groups such as a methyl group, an ethyl group, a propyl group, and a tertiary butyl group, aralkyl groups such as a benzyl group, aryl groups such as a phenyl group, a biphenyl group, a naphthyl group, and a 9,9-dimethylfluorenyl group, heterocyclic groups such as a pyridyl group and a pyrrolyl group, substituted amino groups such as a dimethylamino group, a diethylamino group, a dibenzylamino group, a diphenylamino group, and a ditolylamino group, alkoxyl groups such as a methoxyl group, an ethoxyl group, and a propoxyl group, aryloxy groups such as a phenoxyl group, halogen atoms such as fluorine, chlorine, bromine, and iodine atoms, and a cyano group.

$R_1$ and $R_2$ may be the same as or different from each other.

In formula [1], $R_3$ and $R_4$ each independently represent a hydrogen atom, a substituted or unsubstituted aryl group having three or less rings, or a substituted or unsubstituted heterocyclic group having three or less rings.

Examples of the aryl group having three or less rings represented by $R_3$ and $R_4$ include, but are not limited to, a phenyl group, a naphthyl group, an anthryl group, a phenanthryl group, an indenyl group, a biphenyl group, a terphenyl group, and a fluorenyl group.

Examples of the heterocyclic group having three or less rings represented by $R_3$ and $R_4$ include, but are not limited to, a pyridyl group, a quinolyl group, an oxazolyl group, an oxadiazolyl group, a thiazolyl group, a thiadiazolyl group, a carbazolyl group, an acridinyl group, and a phenanthrolyl group.

Examples of the substituents that may be contained in the aryl group and the heterocyclic group include, but are not limited to, alkyl groups such as a methyl group, an ethyl group, a propyl group, and a tertiary butyl group, aralkyl groups such as a benzyl group, aryl groups such as a phenyl group, a biphenyl group, a naphthyl group, and a 9,9-dimethylfluorenyl group, heterocyclic groups such as a pyridyl group and a pyrrolyl group, substituted amino groups such as a dimethylamino group, a diethylamino group, a dibenzylamino group, a diphenylamino group, and a ditolylamino group, alkoxyl groups such as a methoxyl group, an ethoxyl group, and a propoxyl group, aryloxy groups such as a phenoxyl group, halogen atoms such as fluorine, chlorine, bromine, and iodine atoms, and a cyano group.

One of $R_3$ and $R_4$ represents a substituted or unsubstituted aryl group having three or less rings or a substituted or unsubstituted heterocyclic group having three or less rings.

$R_3$ and $R_4$ may be the same as or different from each other. In this embodiment, in order to achieve good thin film retention property and appropriate energy gap, $R_3$ and $R_4$ may be 9,9-dimethylfluorenyl groups.

The requirements for the constituent material of an organic light-emitting device are that sublimation purification can be utilized as a purification method for increasing the purity of the material and that vacuum vapor deposition can be utilized to form organic compound layers. In conducting sublimation and vacuum deposition, the constituent material of the organic light-emitting device is exposed to a temperature of 300 degrees Celsius or higher in high vacuum of about $10^{-3}$ Pa. When the molecular weight of the constituent material of the organic light-emitting device is more than 1000, the material itself is exposed to a higher temperature condition. As a result, the material may be thermally decomposed and desired physical properties may no longer be obtained. Thus, the heterocyclic compound of this embodiment used as a constituent material of an organic light-emitting device may have a molecular weight of 1000 or less.

Characteristics of the heterocyclic compound of this embodiment will now be described. The heterocyclic compound of this embodiment is a compound that has 4,10-diazachrysene as its basic structure. 4,10-Diazachrysene is a heterocyclic compound that contains nitrogen atoms. In general, nitrogen-containing heterocyclic compounds have high electron affinity because carbon atoms are positively charged due to the high electronegativity of nitrogen atoms. The basic structure, 4,10-diazachrysene, is a fused polycyclic heterocyclic compound having four rings and thus has a larger pi conjugate plane than fused polycyclic heterocyclic compounds having three or less rings, e.g., pyridine, quinoline, and phenanthroline, commonly used as electron transport materials. Accordingly, when the heterocyclic compound of this embodiment is formed into a thin film, stacking of molecules readily occurs and electrons can easily move by interactions with pi electrons. In other words, a thin film composed of the heterocyclic compound of this embodiment has high electron mobility and thus the heterocyclic compound of this embodiment is useful as a constituent material of an electron injection layer or an electron transport layer. An organic light-emitting device that contains the heterocyclic compound of this embodiment as a constituent material of the electron injection layer or the electron transport layer can be driven at a low voltage.

A thin film (spin-coated film) composed of 4,10-diazachrysene and a thin film (spin-coated film) composed of chrysene were prepared by the following process to confirm that the heterocyclic compound of this embodiment has an effect of improving the electron affinity due to incorporation of nitrogen atoms. The HOMO and LUMO levels of these thin films were measured and evaluated. The results are shown in Table 1.

Evaluation of Energy Level 4,10-Diazachrysene was mixed with toluene to prepare a toluene solution having a concentration of 0.1 wt %. The solution was dropped on a glass plate and spin-coating was conducted at 500 RPM for 10 seconds and then at 1000 RPM for 40 seconds to form a thin film (spin-coated film).

Chrysene was mixed with tetrahydrofuran (THF) to prepare a THF solution with a concentration of 0.1 wt %. A thin film was formed by the same process as the thin film of 4,10-diazachrysene.

Ionization potential of the thin films was measured with AC-2 produced by RIKEN KEIKI Co. Ltd., and the observed value with a negative sign was assumed to be the HOMO level of that compound. Next, absorption spectra of the thin films were measured with V-560 produced by JASCO Corporation and energy gaps were calculated. Energy gaps were calculated as the energy of the wavelength at a point of intersection between a tangential line drawn at the long wavelength-side absorption edge of the absorption spectrum and the wavelength axis. The sum of the HOMO level and the energy gap was assumed to be the LUMO level.

TABLE 1

|  | HOMO [eV] | LUMO [eV] | Energy gap [eV] |
|---|---|---|---|
| 4,10-Diazachrysene | −6.07 | −2.80 | 3.27 |
| Chrysene | −5.87 | −2.59 | 3.28 |

As shown in Table 1, 4,10-diazachrysene has about the same energy gap as chrysene but a HOMO level and a LUMO level about 0.2 eV lower than those of chrysene. Thus, when the heterocyclic compound of this embodiment is contained in the electron injection layer or the electron transport layer of an organic light-emitting device, the electron injection from the cathode or adjacent organic compound layer increases and the device can be driven at a low voltage. Moreover, the heterocyclic compound of this embodiment has a high hole-blocking ability. Thus, when the heterocyclic compound is contained in an electron transport layer adjacent to an emission layer, holes can be confined in the emission layer and the emission efficiency can be increased.

However, in the 4,10-diazachrysene backbone, the carbon atoms at the 6- and 12-positions (corresponding to $R_3$ and $R_4$ of formula [1]) have high electron density and their reactivity to electrophilic reactions is highest. Thus, when hydrogen atoms are bonded to the carbon atoms at the 6-position and the 12-position (i.e., when no substituent is introduced), the compound may become decomposed by the electrophilic reaction (oxidation reaction) with singlet molecular oxygen and the like. When the heterocyclic compound of this embodiment is used as an electron injection/transport material and when the heterocyclic compound accepts electrons and turns into anion radicals, the reactivity of the compound itself will presumably increase further. Thus, one of the 6- and 12-positions can be substituted with the aryl group or the heterocyclic group mentioned above.

In the 4,10-diazachrysene backbone, carbon atoms at the 3-position and the 9-position of 4,10-diazachrysene (corresponding to $R_1$ and $R_2$ in formula [1]) are bonded to nitrogen atoms which have an electronegativity higher than that of carbon atoms. Thus, the carbon atoms at the 3-position and the 9-position are more positively charged than other carbon atoms in the backbone. When hydrogen atoms are bonded to the carbon atoms at the 3-position and 9-position carbon atoms, these hydrogen atoms may dissociate by forming $H^+$ (protons), possibly resulting in decomposition of the compound itself. Although such decomposition reactions may be suppressed when the heterocyclic compound of this embodiment is used as the electron injection/transport material, substituents may be introduced into the 3- and 9-positions to further improve the durability of the compound itself. In other words, the alkyl group, the aryl group, or the heterocyclic group described above can be introduced into the 3- and 9-positions.

Introducing an aryl group or a heterocyclic group into one of the 6- and 12-positions of the 4,10-diazachrysene backbone has a large effect on vapor deposition stability during fabrication of an organic light-emitting device and suppression of crystallization in a thin film state in addition to an effect of protecting highly chemically reactive portions.

In general, when organic light-emitting devices that emit blue light (blue light-emitting devices) are used as parts of displays, the blue emission material contained in the blue light-emitting devices has an emission peak in the range of 430 nm to 480 nm. Thus the absorption spectrum of the electron injection/transport material used as a constituent material of a blue light-emitting device must be in the range of 430 nm or less. This is because when the absorption is present in the region exceeding 430 nm, the blue light emitted from the emission layer may be absorbed and the excitation energy of the excitons contained in the emission layer may be resonantly and highly efficiently transferred to the electron transport layer, thereby significantly lowering the emission efficiency.

The energy gap of 4,10-diazachrysene in a thin film state is 3.27 eV (379 nm) as shown in Table 1 above. Thus, even when a substituent is introduced, a sufficient margin is secured relative to the energy gap of the blue region, i.e., 2.88 eV (430 nm). However, when substituents introduced into the 3-, 6-, 9-, and 12-positions are fused polycyclic aromatic groups having four or more rings or fused polycyclic heterocyclic groups having four or more rings, the energy gap of the fused polycyclic aromatic groups having four or more rings or fused polycyclic heterocyclic groups having four or more rings is lower than that of chrysene. Thus, when the fused polycyclic aromatic groups having four or more rings or fused polycyclic heterocyclic groups having four or more rings are introduced into the 4,10-diazachrysene backbone, the bandgap of the compound itself decreases significantly. As a result, the compound itself exhibits blue fluorescence and the absorption will be found in the range of 430 nm or more due to a small Stokes shift. In contrast, a phenyl group and fused polycyclic aromatic groups having three or less rings (naphthyl group, phenanthryl group, and fluorenyl group) are suitable since they have absorptions in regions from ultraviolet to near-ultraviolet. Similarly, monocyclic heterocyclic groups and fused polycyclic heterocyclic groups having three or less rings are suitable since they have absorptions in the regions from ultraviolet to near-ultraviolet.

Therefore, in order to use the heterocyclic compound of this embodiment as an electron injection/transport material and realize a high-efficiency organic light-emitting device, in particular, a high-efficiency blue light-emitting device, a fused polycyclic aromatic group or fused polycyclic heterocyclic group having three or less rings can be introduced into particular positions of the 4,10-diazachrysene backbone.

The heterocyclic compound of this embodiment has an electron injection property since nitrogen atoms contained in the basic structure have electron-withdrawing property. Thus, when the heterocyclic compound of this embodiment is used as a constituent material of an organic light-emitting device, the driving voltage of the device can be lowered. Moreover, since two nitrogen atoms are contained in the basic structure of the heterocyclic compound of this embodiment, the effect of lowering the driving voltage is higher than that of a compound, such as pyridine or quinoline, that has one nitrogen atom in the basic structure.

Specific examples of the heterocyclic compound of this embodiment are as follows. However, the present invention is not limited to these examples.

[Chem. 3]
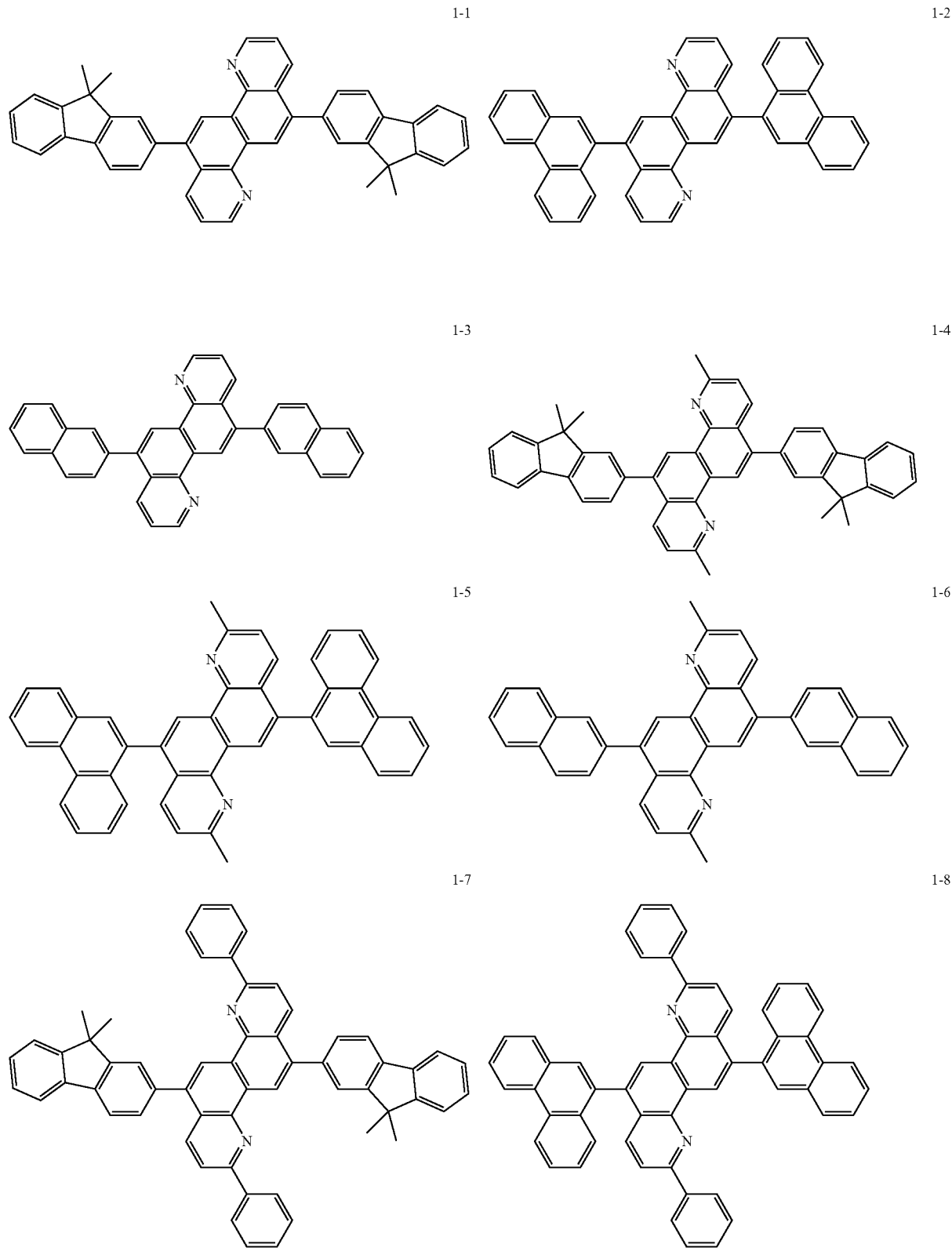

1-9
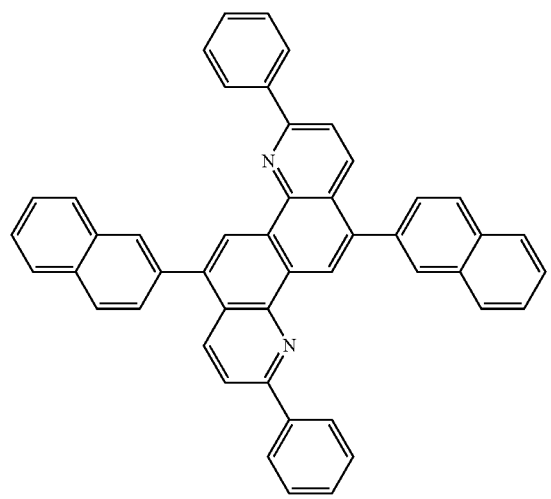
[Chem. 4]
2-1 2-2
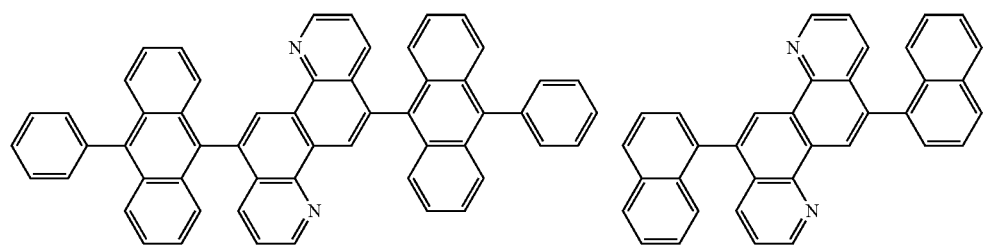
2-3 2-4
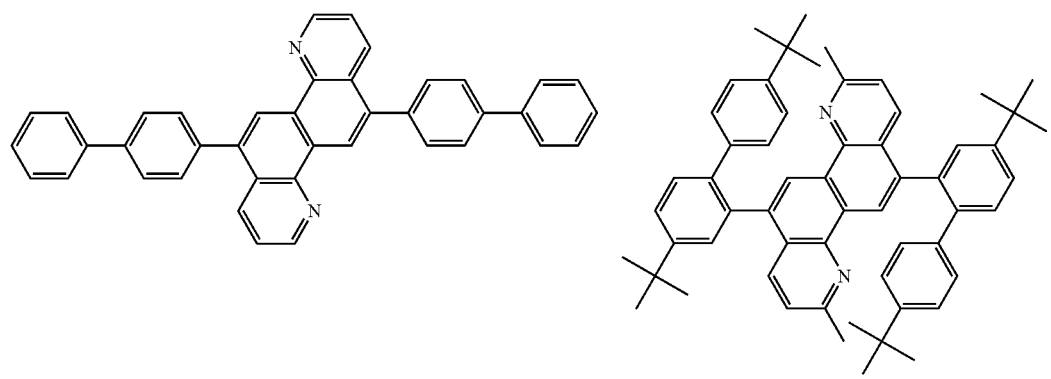

-continued
2-5
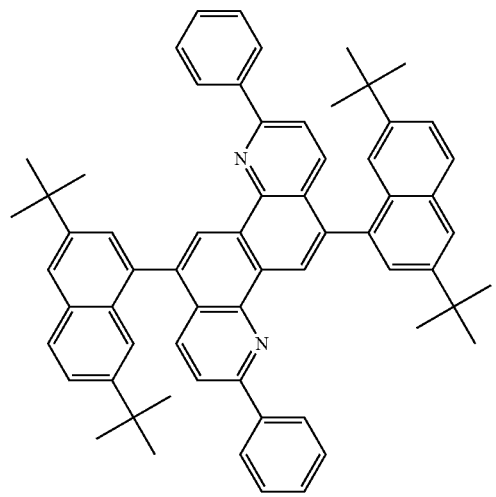
2-6
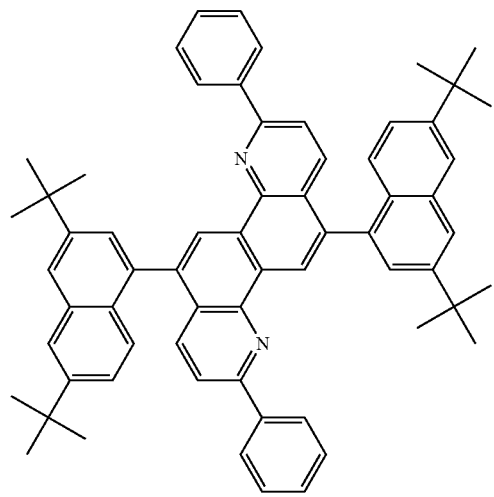
2-7
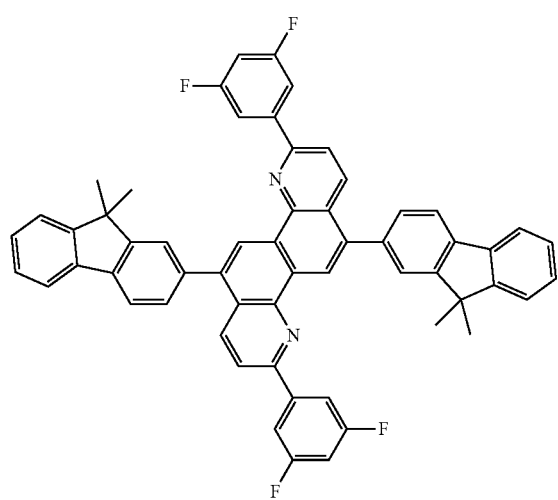
2-8
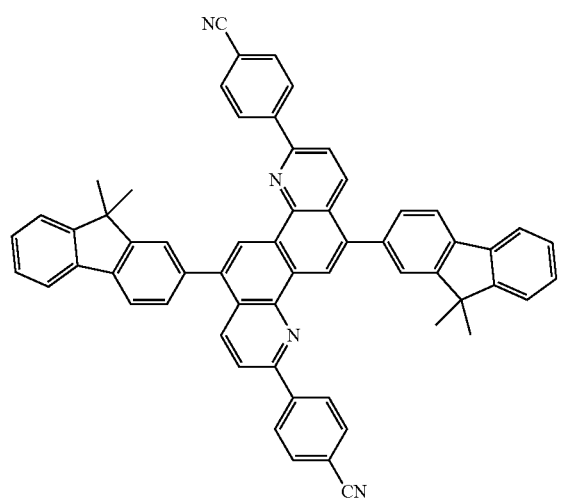
[Chem. 5]
3-1
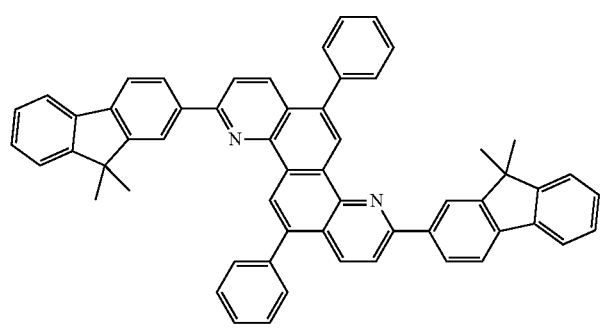
3-2
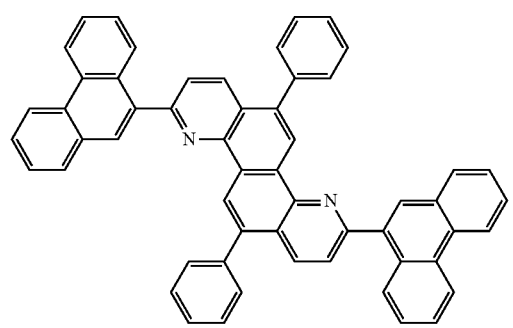

-continued
3-3
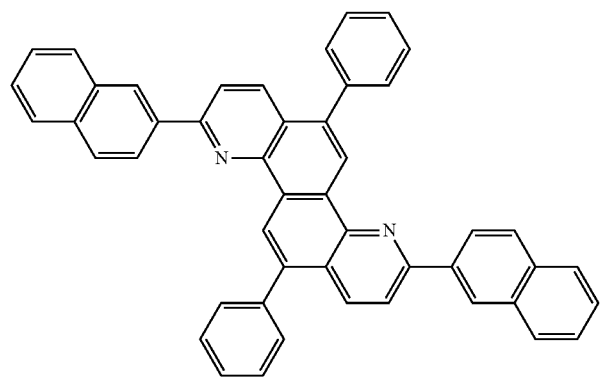
3-4
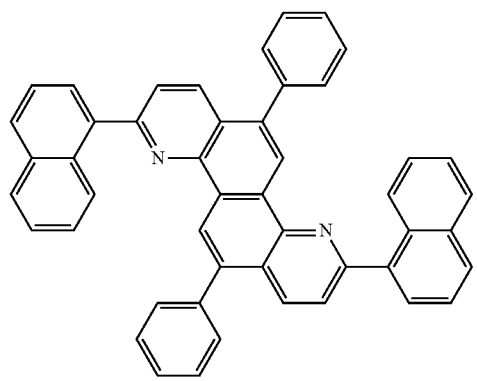
3-5
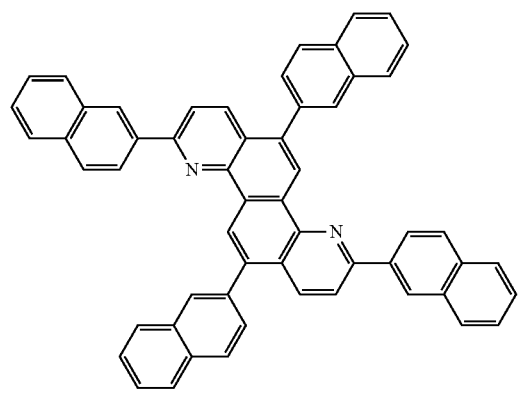
3-6
3-7
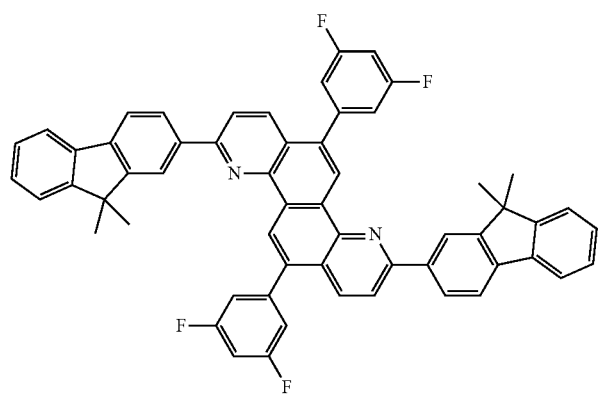
3-8
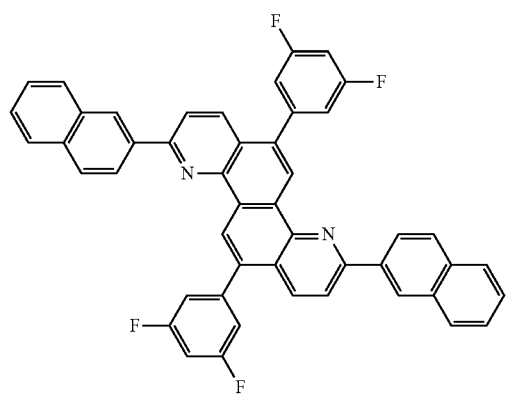
[Chem. 6]
4-1
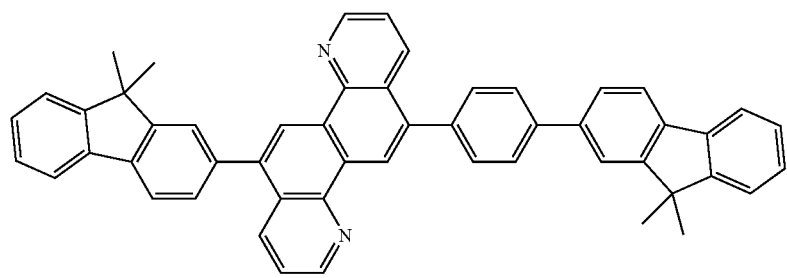

-continued
4-2
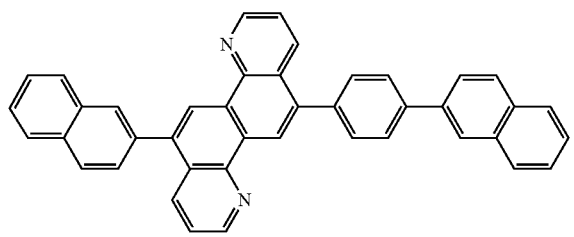
4-3
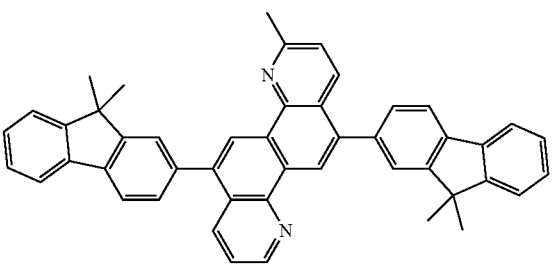
4-4
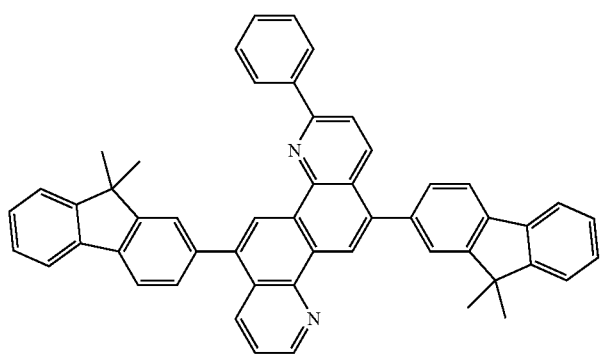
4-5
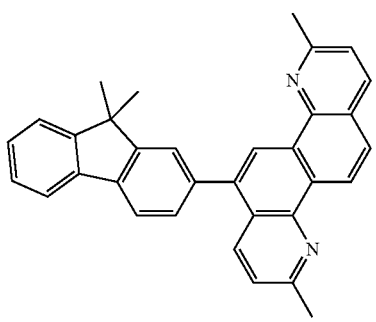
5-1
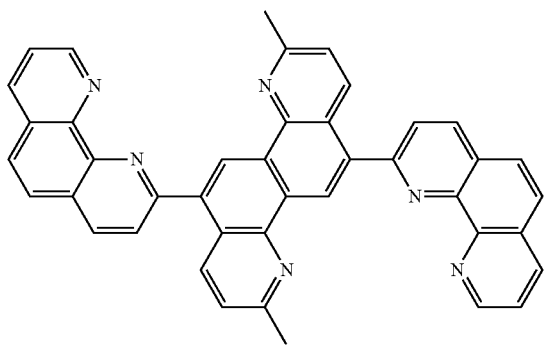
5-2
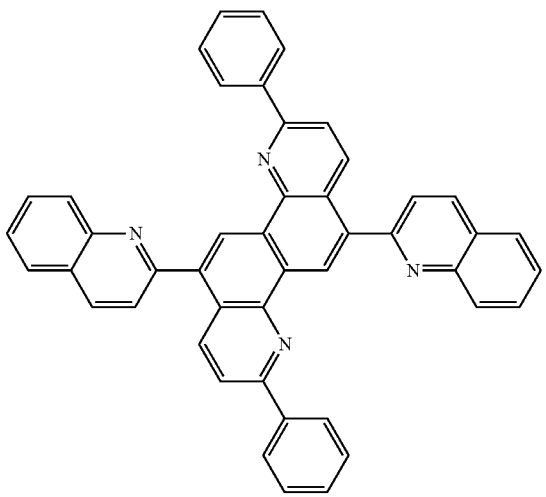
5-3
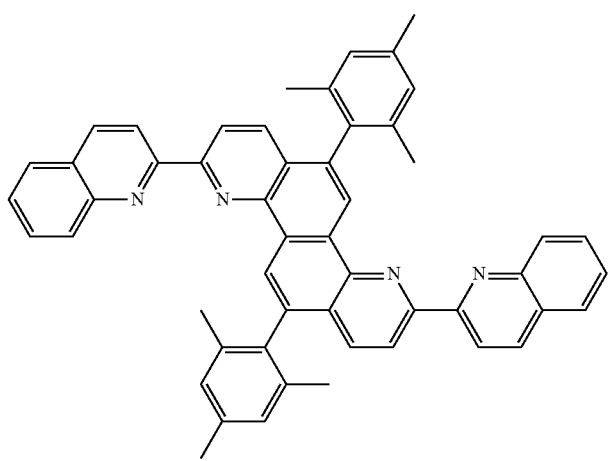

An organic light-emitting device according to an embodiment of the present invention will now be described.

The organic light-emitting device of this embodiment includes an anode, a cathode, and an organic compound layer interposed between the anode and the cathode. One of the anode or the cathode may be transparent or semi-transparent (a transmittance of about 50%) with respect to the emission color. The organic light-emitting device of this embodiment may include an organic compound layer containing the heterocyclic compound described above. The heterocyclic compound can be contained in an electron transport layer or an electron injection layer.

In this embodiment, the electron injection (transport) layer can be composed of the heterocyclic compound only or can be composed of the heterocyclic compound and other electron injection (transport) materials. When an electron injection layer and an electron transport layer are included as the constituent parts of the device, the constituent materials of the electron injection layer and the electron transfer layer can be set as indicated in the table below, for example.

TABLE 2

| Electron transport layer | Electron injection layer |
| --- | --- |
| Heterocyclic compound of the embodiment | (Second) electron injection/transport material |
| (Second) electron injection/transport material | Heterocyclic compound of the embodiment |
| (None) | Heterocyclic compound of the embodiment + (second) electron injection/transport material |
| Heterocyclic compound of the embodiment | Heterocyclic compound of the embodiment + (second) electron injection/transport material |
| Heterocyclic compound of the embodiment + (second) electron injection/transport material | (Third) electron injection/transport material |
| (Second) electron injection/transport material | Heterocyclic compound of the embodiment + (third) electron injection/transport material |

In the organic light-emitting device of this embodiment, the layer structure and the constituent materials are appropriately selected by considering the balance with the carrier mobility of the hole transport material and the difference in the HOMO level and the LUMO level between the host contained in the emission layer and the electron transport material so that the organic light-emitting device will exhibit optimum characteristics. Specific examples of a second electron injection (transport) material used together with the heterocyclic compound of this embodiment will be described below.

Specific structural examples of the organic light-emitting device of this embodiment are described below. These specific examples are merely basic device configurations which do not limit the scope of the present invention.

(1) anode/emission layer/cathode
(2) anode/hole transport layer/electron transport layer/cathode
(3) anode/hole transport layer/emission layer/electron transport layer/cathode
(4) anode/hole injection layer/hole transport layer/emission layer/electron transport layer/cathode
(5) anode/hole injection layer/hole transport layer/emission layer/electron transport layer/cathode
(6) anode/hole transport layer/emission layer/hole-exciton blocking layer/electron transport layer/cathode Various structures other than the structures of (1) to (6) may be employed. For example, an insulating layer, an adhesive layer, or an interference layer may be formed at the interface between an electrode and an organic compound layer. For example, an electron transport layer or a hole transport layer may be constituted by two layers having different ionization potentials.

If needed, the organic light-emitting device can use any other available compound in addition to the organic compound of the embodiment. In particular, the following compounds can be used.

(a) low-molecular-weight and high-molecular-weight hole injection compounds and hole transport compounds
(b) host compounds that serve as the host of the emission layer
(c) light-emitting compounds
(d) electron injection compounds and electron transport compounds Examples of these compounds are described below.

The hole injection compound and the hole transport compound can be materials having high hole mobility. Examples of the low-molecular-weight and high-molecular-weight materials that have functions of injecting and transporting holes include, but are not limited to, triarylamine derivatives, phenylene diamine derivatives, stilbene derivatives, phthalocyanine derivatives, porphyrin derivatives, poly(vinylcarbazole), poly(thiophene), and other electrically conductive polymers. However, the present invention is not limited to these examples.

The heterocyclic compound of this embodiment can also be used as the guest in the emission layer. In such a case, examples of the corresponding host include those compounds indicated in Table 3 below. Derivatives of the compounds shown in Table 3 may also be used.

TABLE 3

H1

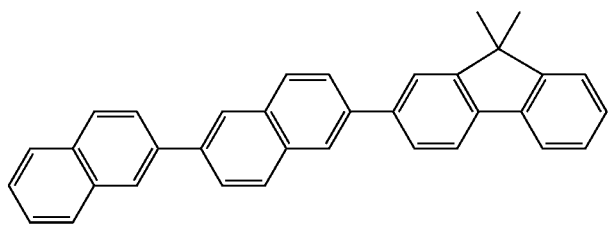 [SMILES: CC1(C)c2ccccc2-c2ccc(-c3ccc4cc(-c5ccc6ccccc6c5)ccc4c3)cc21]

TABLE 3-continued
H2
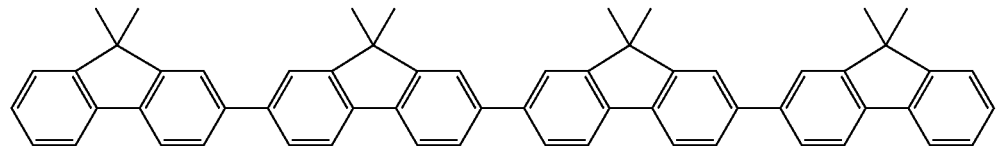 [SMILES: CC1(C)c2ccccc2-c2ccc(-c3ccc4c(c3)C(C)(C)c3cc(-c5ccc6c(c5)C(C)(C)c5cc(-c7ccc8c(c7)C(C)(C)c7ccccc7-8)ccc5-6)ccc3-4)cc21]
H3
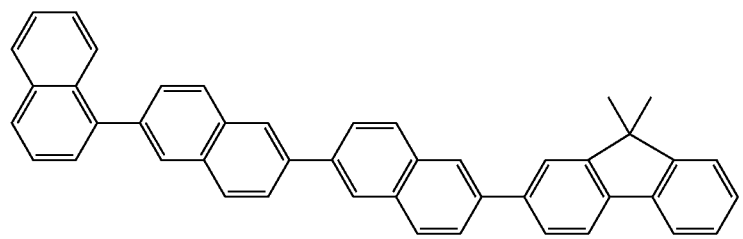 [SMILES: CC1(C)c2ccccc2-c2ccc(-c3ccc4cc(-c5ccc6cc(-c7cccc8ccccc78)ccc6c5)ccc4c3)cc21]
H4
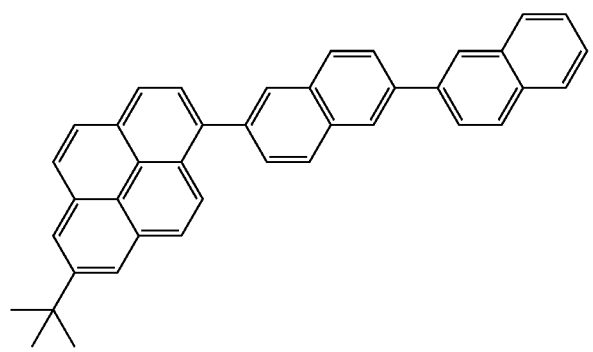 [SMILES: CC(C)(C)c1cc2ccc3ccc(-c4ccc5cc(-c6ccc7ccccc7c6)ccc5c4)c4ccc(c1)c2c34]
H5
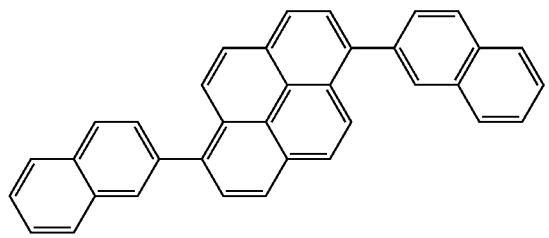 [SMILES: c1ccc2cc(-c3ccc4ccc5c(-c6ccc7ccccc7c6)ccc6ccc3c4c65)ccc2c1]
H6
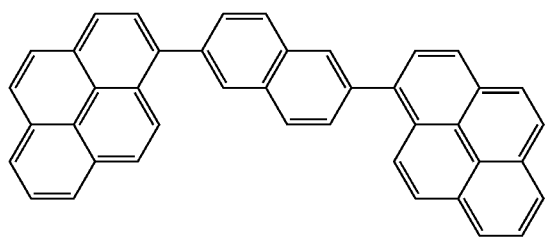 [SMILES: c1cc2ccc3ccc(-c4ccc5cc(-c6ccc7ccc8cccc9ccc6c7c89)ccc5c4)c4ccc(c1)c2c34]

TABLE 3-continued
H7
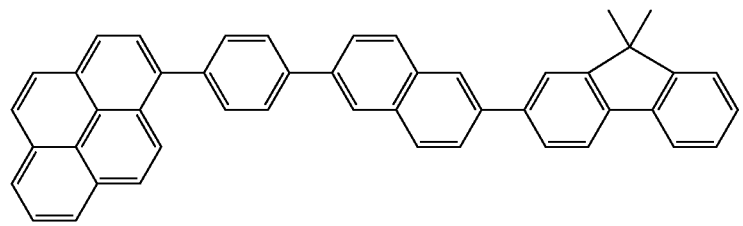 [SMILES: CC1(C)c2ccccc2-c2ccc(-c3ccc4cc(-c5ccc(-c6ccc7ccc8cccc9ccc6c7c89)cc5)ccc4c3)cc21]
H8
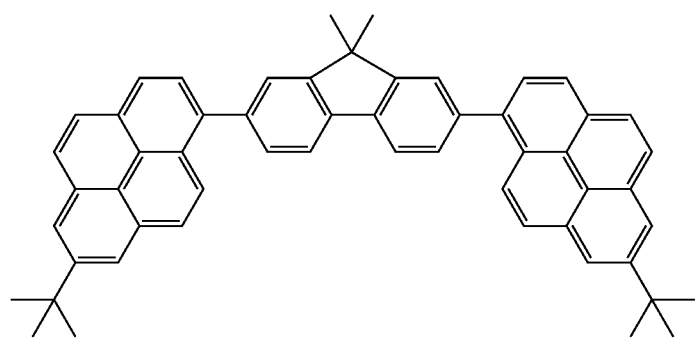 [SMILES: CC(C)(C)c1cc2ccc3ccc(-c4ccc5c(c4)C(C)(C)c4cc(-c6ccc7ccc8cc(C(C)(C)C)cc9ccc6c7c89)ccc4-5)c4ccc(c1)c2c34]
H9
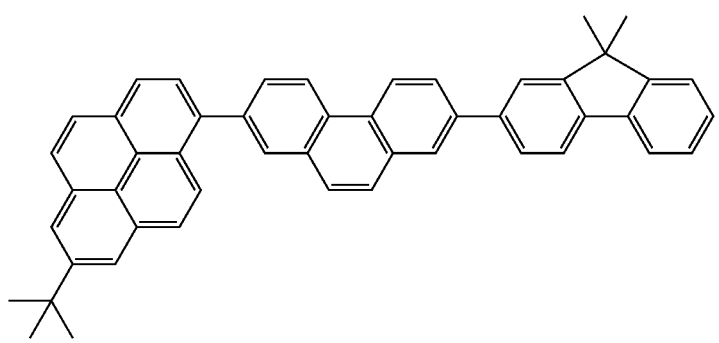 [SMILES: CC(C)(C)c1cc2ccc3ccc(-c4ccc5c(ccc6cc(-c7ccc8c(c7)C(C)(C)c7ccccc7-8)ccc65)c4)c4ccc(c1)c2c34]
H10
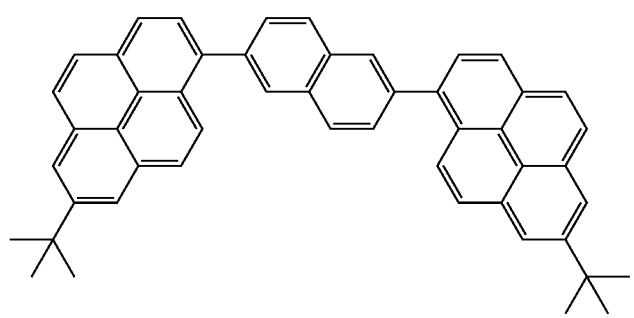 [SMILES: CC(C)(C)c1cc2ccc3ccc(-c4ccc5cc(-c6ccc7ccc8cc(C(C)(C)C)cc9ccc6c7c89)ccc5c4)c4ccc(c1)c2c34]

TABLE 3-continued
H11
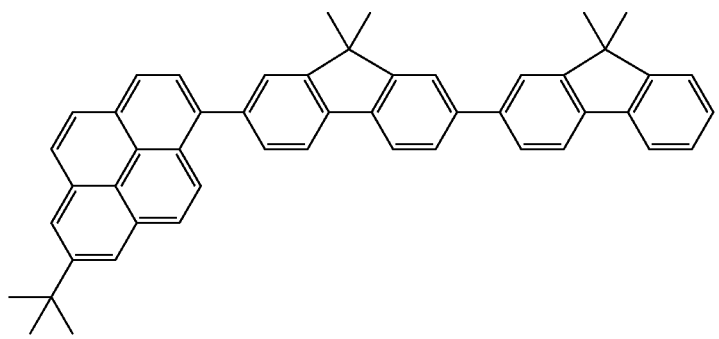 [SMILES: CC(C)(C)c1cc2ccc3ccc(-c4ccc5c(c4)C(C)(C)c4cc(-c6ccc7c(c6)C(C)(C)c6ccccc6-7)ccc4-5)c4ccc(c1)c2c34]
H12
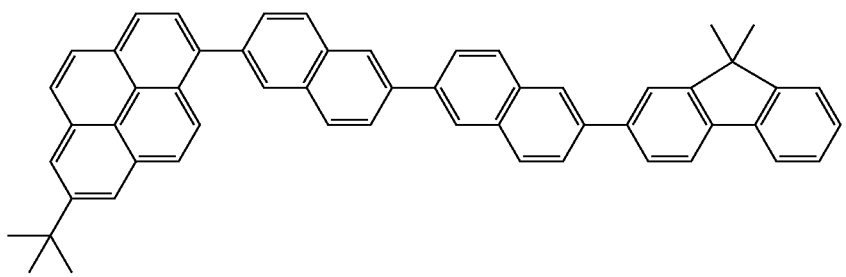 [SMILES: CC(C)(C)c1cc2ccc3ccc(-c4ccc5cc(-c6ccc7cc(-c8ccc9c(c8)C(C)(C)c8ccccc8-9)ccc7c6)ccc5c4)c4ccc(c1)c2c34]
H13
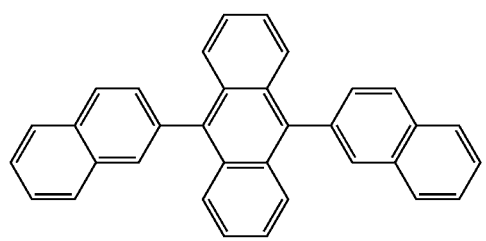 [SMILES: c1ccc2cc(-c3c4ccccc4c(-c4ccc5ccccc5c4)c4ccccc34)ccc2c1]
H14
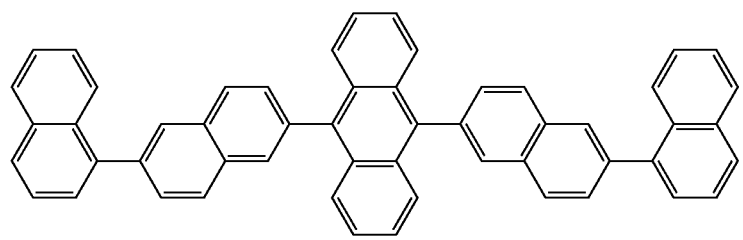 [SMILES: c1ccc2c(-c3ccc4cc(-c5c6ccccc6c(-c6ccc7cc(-c8cccc9ccccc89)ccc7c6)c6ccccc56)ccc4c3)cccc2c1]
H15
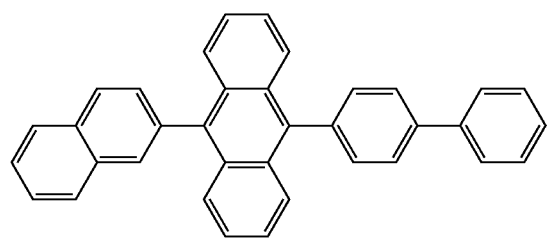 [SMILES: c1ccc(-c2ccc(-c3c4ccccc4c(-c4ccc5ccccc5c4)c4ccccc34)cc2)cc1]

TABLE 3-continued
H16
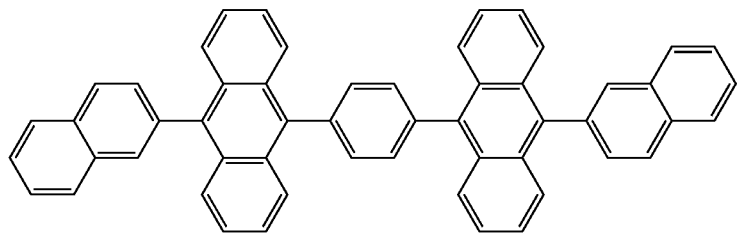 [SMILES: c1ccc2cc(-c3c4ccccc4c(-c4ccc(-c5c6ccccc6c(-c6ccc7ccccc7c6)c6ccccc56)cc4)c4ccccc34)ccc2c1]
H17
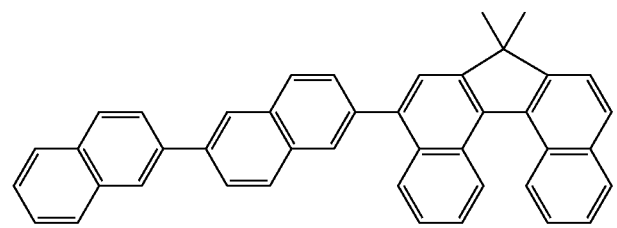 [SMILES: CC1(C)c2ccc3ccccc3c2-c2c1cc(-c1ccc3cc(-c4ccc5ccccc5c4)ccc3c1)c1ccccc21]
H18
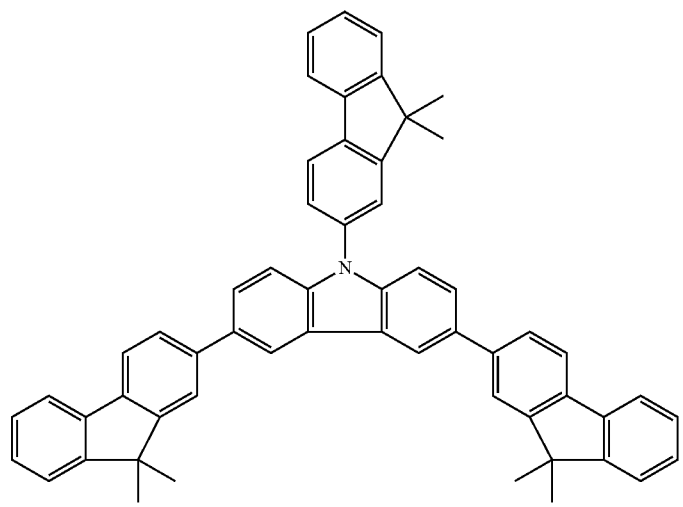 [SMILES: CC1(C)c2ccccc2-c2ccc(-c3ccc4c(c3)c3cc(-c5ccc6c(c5)C(C)(C)c5ccccc5-6)ccc3n4-c3ccc4c(c3)C(C)(C)c3ccccc3-4)cc21]
H19
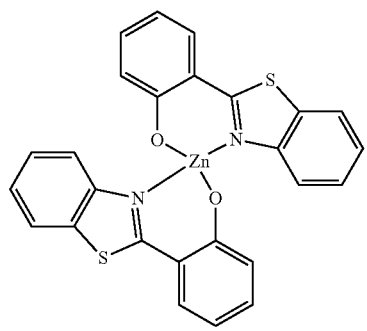

TABLE 3-continued
H20
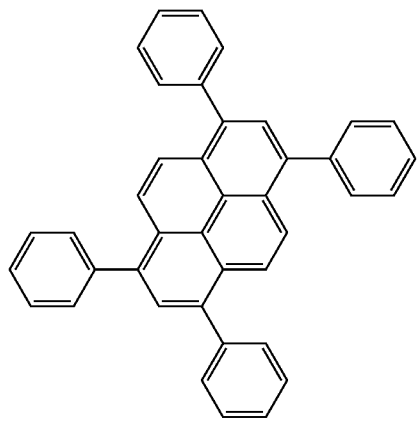 [SMILES: c1ccc(-c2cc(-c3ccccc3)c3ccc4c(-c5ccccc5)cc(-c5ccccc5)c5ccc2c3c54)cc1]
H21
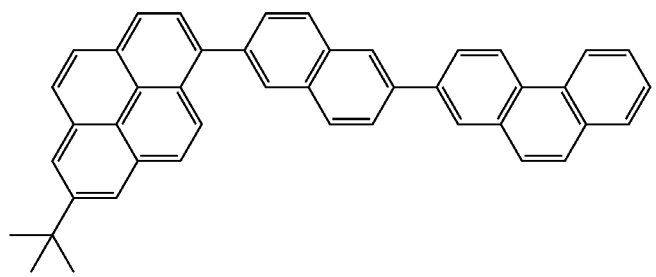 [SMILES: CC(C)(C)c1cc2ccc3ccc(-c4ccc5cc(-c6ccc7c(ccc8ccccc87)c6)ccc5c4)c4ccc(c1)c2c34]
H22
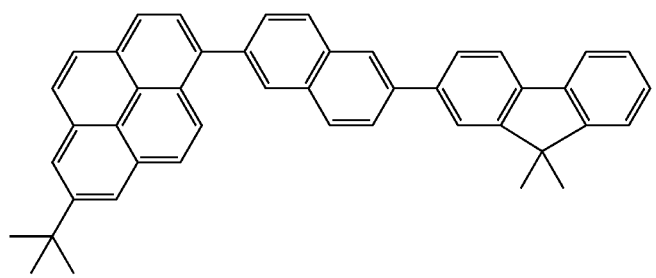 [SMILES: CC(C)(C)c1cc2ccc3ccc(-c4ccc5cc(-c6ccc7c(c6)C(C)(C)c6ccccc6-7)ccc5c4)c4ccc(c1)c2c34]
H23
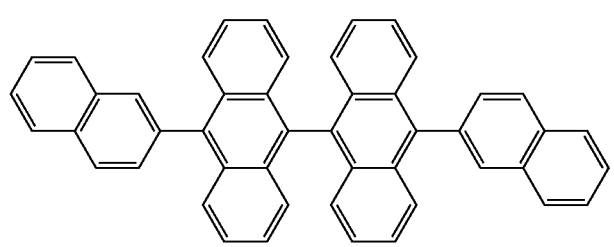 [SMILES: c1ccc2cc(-c3c4ccccc4c(-c4c5ccccc5c(-c5ccc6ccccc6c5)c5ccccc45)c4ccccc34)ccc2c1]
H24
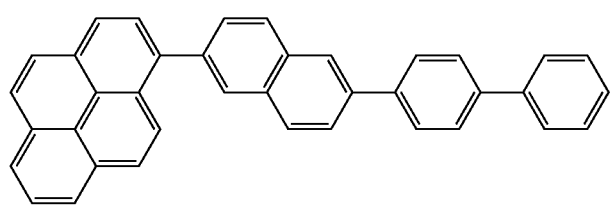 [SMILES: c1ccc(-c2ccc(-c3ccc4cc(-c5ccc6ccc7cccc8ccc5c6c78)ccc4c3)cc2)cc1]

TABLE 3-continued

H25

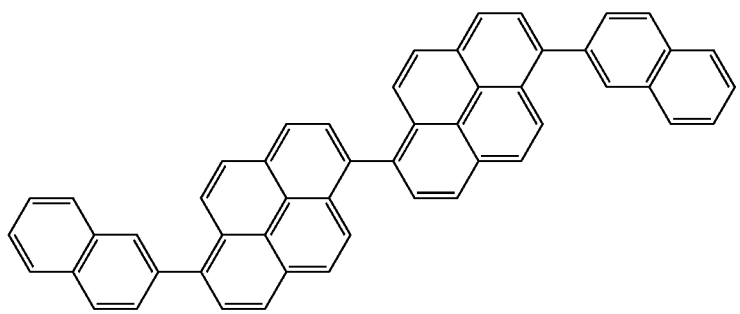 [SMILES: c1ccc2cc(-c3ccc4ccc5c(-c6ccc7ccc8c(-c9ccc%10ccccc%10c9)ccc9ccc6c7c98)ccc6ccc3c4c65)ccc2c1]

H26

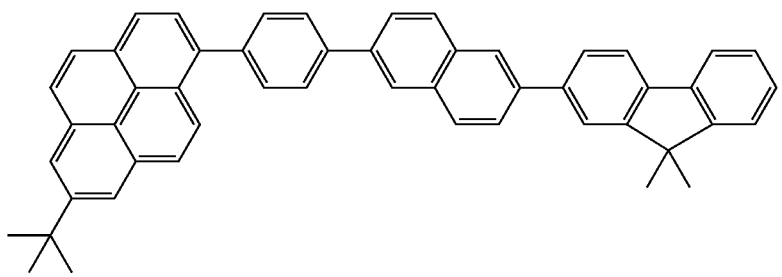 [SMILES: CC(C)(C)c1cc2ccc3ccc(-c4ccc(-c5ccc6cc(-c7ccc8c(c7)C(C)(C)c7ccccc7-8)ccc6c5)cc4)c4ccc(c1)c2c34]

H27

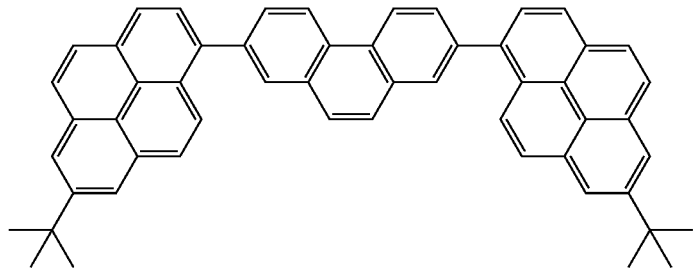 [SMILES: CC(C)(C)c1cc2ccc3ccc(-c4ccc5c(ccc6cc(-c7ccc8ccc9cc(C(C)(C)C)cc%10ccc7c8c9%10)ccc65)c4)c4ccc(c1)c2c34]

H28

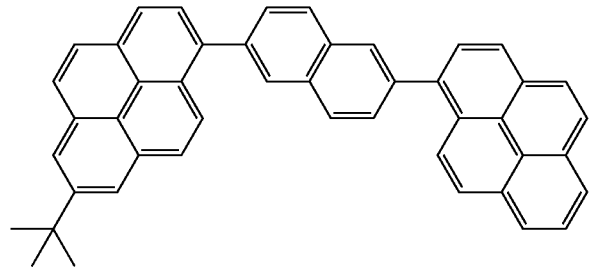 [SMILES: CC(C)(C)c1cc2ccc3ccc(-c4ccc5cc(-c6ccc7ccc8cccc9ccc6c7c89)ccc5c4)c4ccc(c1)c2c34]

Other examples of the host compound include fused ring compounds (e.g., fluorene derivatives, naphthalene derivatives, anthracene derivatives, pyrene derivatives, carbazole derivatives, quinoxaline derivatives, and quinoline derivatives), organic aluminum complexes such as tris(8-quinolinolato)aluminum, organic zinc complexes, and polymer derivatives such as triphenylamine derivatives, poly(fluorene) derivatives, and poly(phenylene) derivatives. However, the present invention is not limited to these examples.

The electron injection compound and the electron transport compound are appropriately selected by considering, for example, the balance with the hole mobility of the hole injection compound and the hole transport compound. Examples of the compounds that have functions of injecting and transporting electrons other than the heterocyclic compound of this embodiment include, but are not limited to, oxadiazole derivatives, oxazole derivatives, pyrazine derivatives, triazole derivatives, triazine derivatives, quinoline derivatives, quinoxaline derivatives, phenanthroline derivatives, and organic aluminum complexes.

The constituent material of the anode can have a large work function. Examples thereof include single metals such as gold, platinum, silver, copper, nickel, palladium, cobalt, selenium, vanadium, and tungsten, alloys of two or more of these single metals, and metal oxides such as tin oxide, zinc oxide, indium oxide, indium tin oxide (ITO), and indium zinc oxide. Electrically conductive polymers such as polyaniline, polypyrrole, and polythiophene can also be used. These electrode substances may be used alone or in combination. The anode may be constituted by single layer or two or more layers.

In contrast, the material of the cathode can have a small work function. Examples of the cathode material include single metals such as alkali metals, e.g., lithium, alkaline earth metals, e.g., calcium, aluminum, titanium, manganese, silver, lead, and chromium. Alloys of two or more of these single metals can also be used. For example, magnesium-silver, aluminum-lithium, and aluminum-magnesium can be used. Metal oxides such as indium tin oxide (ITO) can also be used. These electrode substances may be used alone or in combination. The cathode may be constituted by single layer or two or more layers.

In the organic light-emitting device according to this embodiment, a layer that contains the organic compound of this embodiment and layers composed of other organic compounds are formed by the following method. Typically, thin films are formed by vacuum vapor deposition, ionized evaporation, sputtering, plasma, or a coating technique in which a material is dissolved in an appropriate solvent (e.g., spin-coating, dipping, casting, a Langmuir-Blodgett technique, and an ink jet technique). When layers are formed by vacuum vapor deposition or a solution coating technique, crystallization does not readily occur and stability overtime is improved. When a coating technique is used to form films, an appropriate binder resin may be used in combination to form films.

Examples of the binder resin include, but are not limited to, polyvinyl carbazole resins, polycarbonate resins, polyester resins, ABS resins, acrylic resins, polyimide resins, phenol resins, epoxy resins, silicone resins, and urea resins. These binder resins may be used alone as a homopolymer or in combination as a copolymer. If necessary, additives such as plasticizers, antioxidants, and UV absorbers may be used together.

The organic light-emitting device of this embodiment can be used in display apparatuses and lighting apparatuses. The organic light-emitting device can also be used as the exposure light source of an electrophotographic image-forming apparatus or a backlight of a liquid crystal display apparatus.

When the organic light-emitting device of this embodiment is used as a component of a display apparatus, the organic light-emitting device is installed in a display unit. The display unit includes plural pixels and the organic light-emitting device of this embodiment is installed in each pixel. The display apparatus also includes a unit that supplies electrical signals to the organic light-emitting device. The display apparatus can also be used as an image display apparatus of a personal computer or the like.

The display apparatus may be used in a display unit of an imaging apparatus such as a digital camera and a digital video camera. An imaging apparatus is an apparatus that includes a display unit and an imaging unit that includes an imaging optical system for capturing images.

An image display apparatus equipped with the organic light-emitting device of this embodiment will now be described.

FIG. 1 is a schematic cross-sectional view showing an example of an image display apparatus equipped with the organic light-emitting device of this embodiment.

An image display apparatus 1 shown in FIG. 1 includes a substrate 11 such as a glass substrate and a moisture-proof film 12 on the substrate 11. The moisture-proof film 12 protects a TFT or organic compound layers. A gate electrode 13 composed of chromium or the like is formed on the moisture-proof film 12. A gate insulating film 14 is formed over the gate electrode 13. A semiconductor layer 15 is formed over the gate insulating film 14.

A TFT element 18 includes the semiconductor layer 15, a drain electrode 16, and a source electrode 17. An insulating film 19 is provided on the top of the TFT element 18. The source electrode 17 is connected to an anode 111 of the organic light-emitting device through a contact hole (through hole) 110.

Although an organic compound layer 112 is illustrated as a single layer shown in FIG. 1, the organic compound layer 112 is actually a laminate constituted by two or more layers. In order to suppress deterioration of the organic light-emitting device, a first protective layer 114 and a second protective layer 115 are formed on a cathode 113.

The luminance of the emission from the organic light-emitting device is controlled by electric signals supplied from the TFT element 18. Since plural light-emitting devices are provided on the surface, an image can be displayed by controlling the emission luminance of the respective light-emitting devices.

When a display apparatus using the organic light-emitting devices of the embodiment is driven, high-quality images can be stably displayed over a long time.

EXAMPLES

The present invention will now be described by using non-limiting examples.

Example 1

Synthesis of Example Compound 1-1

Example compound 1-1 was synthesized by the following process.

(1) Synthesis of 4,10-diazachrysene 4,10-Diazachrysene was synthesized in accordance with a procedure described in NPL 1, pp. 88 to 89, "2.1. Materials".

(2) Synthesis of Intermediate Compound 1

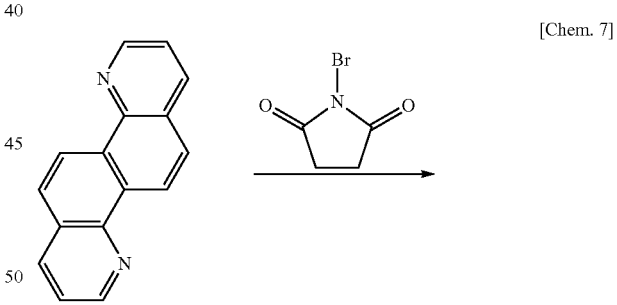

[Chem. 7]

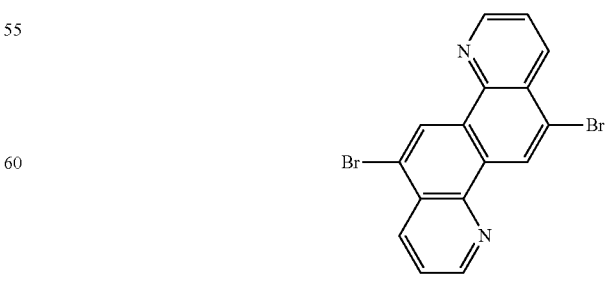

Intermediate compound 1

After 4,10-diazachrysene (3.00 g, 13.0 mmol) was dissolved in concentrated sulfuric acid (20 ml), N-bromosuccinimide (5.10 g, 28.7 mmol) was added to the resulting solution. The reaction solution was then stirred for 2 hours under heating on a silicone oil bath heated to 70 degrees Celsius. After the reaction solution was cooled to room temperature, the reaction solution was slowly poured into 300 g of ice and the resulting yellow solution was neutralized with 28% ammonia water. Gray solids precipitated by neutralization with ammonia water were filtered. The gray solids were washed with water and then methanol and vacuum dried at 80 degrees Celsius to obtain a crude product. The crude product was recrystallized with a chlorobenzene/methanol system. White solids generated by the recrystallization was vacuum dried at 80 degrees Celsius to obtain 4.14 g (yield: 82%) of an intermediate compound 1.

(3) Synthesis of Example Compound 1-1

[Chem. 8]

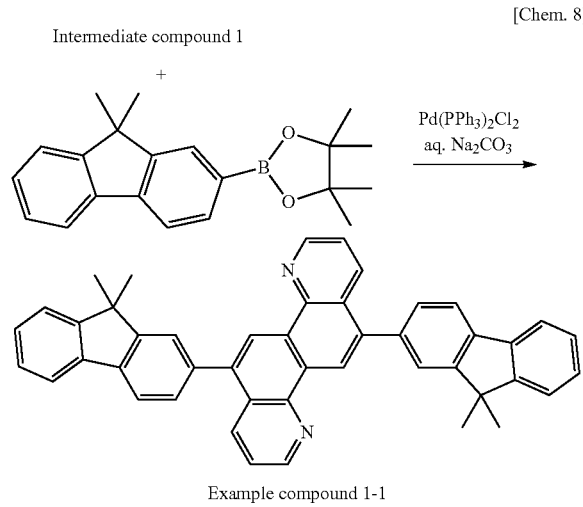

Example compound 1-1

Following compounds are charged into a reactor in a nitrogen atmosphere and dissolved in a mixed solvent containing toluene (20 ml) and ethanol (2 ml) under heating:

intermediate compound 1: 0.100 g (0.258 mmol) 2-(9,9-dimethylfluoren-2-yl)-4,4,5,5-tetramethyl-1,3,2-dioxaborolane: 0.182 g (0.568 mmol)

Pd(PPh$_3$)$_2$Cl$_2$: 0.0181 g (0.0258 mmol)

To the reaction solution, an aqueous solution containing 0.120 g (1.14 mmol) sodium carbonate and 1 ml distilled water was added, and the reaction solution was stirred for 12 hours under heating on a silicone oil bath heated to 90 degrees Celsius.

After the reaction solution was cooled to room temperature, water, toluene, and ethyl acetate were added and the solvent was extracted to isolate an organic layer from a water layer. Next, a toluene/ethyl acetate mixed solvent was added to the water layer to conduct second and third solvent extractions. The resulting organic layer was added to the organic layer solution obtained by the first solvent extraction. The organic layer was washed with saturated saline and dried over sodium sulfate. The solvent was distilled away under a reduced pressure to obtain a crude product. The crude product was purified by silica gel column chromatography (developing solvent: chloroform/heptane=3/1) to obtain crystals. The crystals were vacuum dried at 120 degrees Celsius and purified by sublimation to obtain 0.111 g (yield: 70%) of example compound 1-1.

Matrix-assisted laser desorption ionization-time of flight mass spectrometry (MALDI-TOF MS) was conducted to confirm 614.3, which is M$^+$ of this compound.

$^1$H-NMR measurement was conducted to confirm the structure of this compound.

$^1$H-NMR (CDCl$_3$, 500 MHz) d (ppm): 9.51 (2H, s), 9.11 (2H, dd), 8.50 (2H, dd), 7.91 (2H, d), 7.84 (2H, dd), 7.73 (2H, bs), 7.63 (2H, dd), 7.59-7.56 (2H, m), 7.51 (2H, dd), 7.43-7.37 (4H, m), 1.61 (12H, s)

Example 2

An organic light-emitting device including an anode, a hole transport layer, an emission layer, an electron transport layer, an electron injection layer, and a cathode sequentially stacked on a substrate in that order was prepared by the following method.

A film of indium tin oxide (ITO) was formed on a glass substrate by sputtering to form an anode. The thickness of the anode was 120 nm. The substrate with the anode was ultrasonically washed with acetone and then isopropyl alcohol (IPA) and then washed with pure water, followed by drying. UV/ozone washing followed. The resulting processed substrate was used as a transparent electrically conductive supporting substrate.

Compound A indicated below serving as a hole transport material was mixed with chloroform to prepare a chloroform solution having a solute concentration of 0.1 wt %.

Compound A

[Chem. 9]

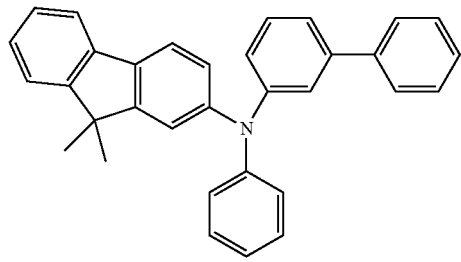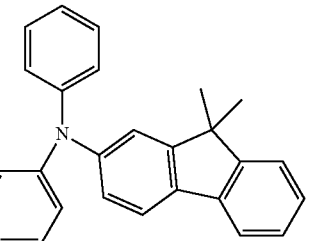

The chloroform solution was dropped on the anode and spin-coating was conducted at 500 RPM for 10 seconds and then at 1000 RPM for 40 seconds to form a film. The film was dried under heating for 10 minutes in a vacuum oven at 80 degrees Celsius to completely remove the solvent herein and to thereby form a hole transport layer. The thickness of the hole transport layer was 40 nm.

Next, compound B and compound C indicated below were co-deposited on the hole transport layer to form an emission layer. The degree of vacuum during deposition was $1.0 \times 10^{-4}$ Pa and the deposition rate was set to 0.1 nm/sec or more and 0.2 nm/sec or less. The mixing ratio of compound B to compound C in the emission layer was adjusted to 95:5 on a weight basis. The thickness of the emission layer was 30 nm.

[Chem. 10]

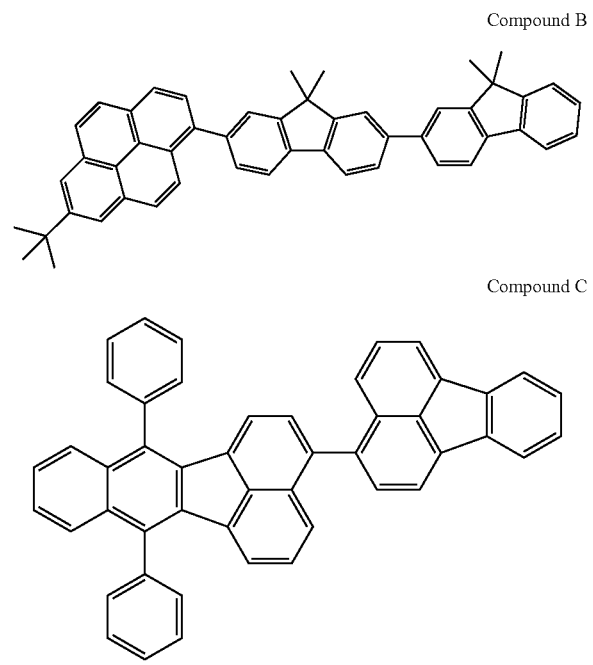

Compound B

Compound C

Next, example compound 1-1 was formed into a film on the emission layer by vacuum vapor deposition to form an electron transport layer. The thickness of the electron transport layer was set to 30 nm, the degree of vacuum during deposition was set to $1.0 \times 10^{-4}$ Pa, and the deposition rate was set to 0.1 nm/sec or more and 0.2 nm/sec or less.

A film of lithium fluoride (LiF) was formed on the electron transport layer by vacuum vapor deposition to form an electron injection layer. The thickness of the electron injection layer was set to 0.5 nm, the degree of vacuum during deposition was set to $1.0 \times 10^{-4}$ Pa, and the deposition rate was set to 0.01 nm/sec. Next, an aluminum film was formed on the electron injection layer by vacuum vapor deposition to form a cathode. The thickness of the cathode was set to 100 nm, the degree of vacuum during deposition was set to $1.0 \times 10^{-4}$ Pa, and the deposition rate was set to 0.5 nm/sec or more and 1.0 nm/sec or less.

Lastly, a protective glass plate was placed in a dry air atmosphere to prevent deterioration of the organic light-emitting device by adsorption of moisture, and the device was sealed with an acrylic resin adhesive. An organic light-emitting device was obtained as such.

The properties of the resulting organic light-emitting devices were measured and evaluated. In particular, the current-voltage characteristic was measured with a microammeter 4140B produced by Hewlett-Packard Co., and the emission luminance was measured with BM7 produced by TOPTON CORPORATION. As a result, excellent blue emission with an emission luminance of 376 cd/m² was observed under application of a voltage of 4.0 V. A voltage was applied to this device for 100 hours in a nitrogen atmosphere. Continuation of satisfactory emission was confirmed.

The present invention provides a heterocyclic compound that enables low-voltage driving and high-efficiency high-luminance optical output and that offers high durability, and an organic light-emitting device including the heterocyclic compound. The heterocyclic compound also has high electron affinity, electron transfer property, and stability. The organic light-emitting device thus also enables low-voltage driving and high-efficiency high-luminance optical output and offers high durability.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2009-194110, filed Aug. 25, 2009, which is hereby incorporated by reference herein in its entirety.

The invention claimed is:

1. A heterocyclic compound represented by general formula [1]:

[Chem. 1]

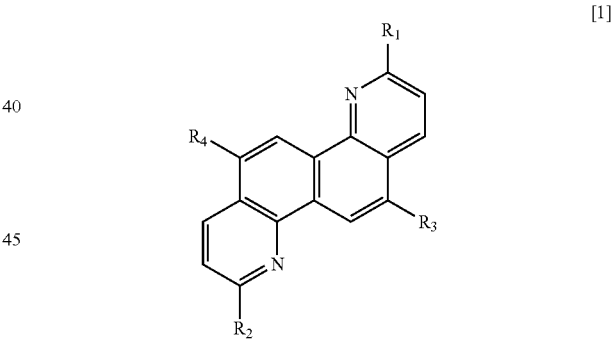

[1]

(wherein $R_1$ and $R_2$ each independently represent a hydrogen atom, a substituted or unsubstituted alkyl group, a substituted or unsubstituted aryl group having three or less rings, or a substituted or unsubstituted heterocyclic group having three or less rings; $R_1$ and $R_2$ may be the same as or different from each other; $R_3$ and $R_4$ each independently represent a hydrogen atom, a substituted or unsubstituted aryl group having three or less rings, or a substituted or unsubstituted heterocyclic group having three or less rings; one of $R_3$ and $R_4$ represents a substituted or unsubstituted aryl group having three or less rings or a substituted or unsubstituted heterocyclic group having three or less rings; and $R_3$ and $R_4$ may be the same as or different from each other).

2. The heterocyclic compound according to claim 1, wherein $R_3$ and $R_4$ each represent a 2-(9,9-dimethyl)fluorenyl group.

3. An organic light-emitting device comprising:
an anode;
a cathode; and
an organic compound layer interposed between the anode and the cathode,
wherein the organic compound layer contains the heterocyclic compound according to claim 1.

4. The organic light-emitting device according to claim 3, wherein the organic compound layer containing the heterocyclic compound is an electron injection layer or an electron transport layer.

5. An image display apparatus comprising:
a plurality of pixels each including the organic light-emitting device according to claim 3; and
a unit configured to supply electrical signals to the organic light-emitting device.

* * * * *